United States Patent
Kawano

[11] Patent Number: 6,146,364
[45] Date of Patent: Nov. 14, 2000

[54] MEDICAL DEVICE HAVING A BRANCH AND PROCESS FOR PRODUCING THE SAME

[75] Inventor: Takumi Kawano, Tokyo, Japan

[73] Assignee: Kawasumi Laboratories, Inc., Tokyo, Japan

[21] Appl. No.: 09/398,197

[22] Filed: Sep. 17, 1999

Related U.S. Application Data

[62] Division of application No. 08/991,211, Dec. 16, 1997, Pat. No. 6,022,441.

[30] Foreign Application Priority Data

| Dec. 27, 1996 | [JP] | Japan | 8-358196 |
| Jan. 13, 1997 | [JP] | Japan | 9-015873 |
| Aug. 8, 1997 | [JP] | Japan | 9-227373 |

[51] Int. Cl.[7] .......................... A61M 25/00; A61M 25/16
[52] U.S. Cl. .......................................... 604/284; 604/533
[58] Field of Search ..................... 604/513, 523, 604/533, 539, 284; 156/244.13; 138/155; 285/125.1, 131.1, 132.1, 133.11

[56] References Cited

U.S. PATENT DOCUMENTS

| 3,291,670 | 12/1966 | Usab. | |
| 3,502,357 | 3/1970 | Wagner. | |
| 3,833,940 | 9/1974 | Hartenbach | 604/284 |
| 4,142,528 | 3/1979 | Whelan, Jr. et al. | 604/284 |
| 4,767,478 | 8/1988 | Christine | 156/69 |
| 4,790,832 | 12/1988 | Lopez | 604/283 |
| 4,797,246 | 1/1989 | Reinke et al. | 264/504 |
| 4,873,048 | 10/1989 | Jarvenkyla | 264/504 |
| 5,116,327 | 5/1992 | Seder et al. | 604/284 |
| 5,125,915 | 6/1992 | Berry et al. | 604/283 |
| 5,273,533 | 12/1993 | Bonaldo | 604/83 |
| 5,352,215 | 10/1994 | Thome et al. | 604/284 |
| 5,387,015 | 2/1995 | Sisk | 285/55 |
| 5,549,554 | 8/1996 | Miraki | 604/101 |
| 5,807,356 | 9/1998 | Finch, Jr. et al. | 604/284 |
| 6,022,441 | 2/2000 | Kawano | 156/244.13 |

FOREIGN PATENT DOCUMENTS

| 2 046 535 | 2/1969 | France | B29C 27/00 |
| 2 033 178 | 2/1985 | France | B29C 27/00 |
| 705 207 | 4/1941 | Germany. | |
| 1 479 153 | 11/1965 | Germany. | |
| 1 536 019 | 11/1969 | Germany. | |
| 33 27 256 | 2/1985 | Germany | A61M 16/00 |
| 44 10 909 | 10/1995 | Germany | B65B 61/18 |
| 62-135344 | 6/1987 | Japan | B29C 63/34 |
| 7-124249 | 5/1995 | Japan | A61M 1/14 |
| 6905332 | 4/1969 | Netherlands | B29D 23/20 |

*Primary Examiner*—Sharon Kennedy
*Attorney, Agent, or Firm*—Sughrue, Mion, Zinn, Macpeak & Seas, PLLC

[57] ABSTRACT

A process for producing a medical device having a branch includes the steps of: welding a bottom of the tubular member on a mounting surface of a constituent material of a main tube extruded under elevated temperature, welding firmly the bottom of the tubular member to the mounting surface of the main tube while aspirating the constituent material of the main tube from above the tubular member, forming a hole in the mounting surface of the main tube so as to communicate an interior of the tubular member with an interior of the main tube, and cutting the main tube, thereby assembling the medical device having the branch.

6 Claims, 22 Drawing Sheets

MEDICAL DEVICE HAVING A BRANCH AND PROCESS FOR PRODUCING THE SAME

This is a divisional of application Ser. No. 08/991,211 filed Dec. 16, 1997, now U.S. Pat. No. 6,022,441, the disclosure of which is incorporated herein by reference.

BACKGROUND OF THE INVENTION

1. Field of the Invention

The present invention relates to a medical device having a main tube which has a branch (e.g. Y and T tubes) connected to a branchline tube (for injecting medical fluids into the main tube and for monitoring the pressure on the main tube). The invention also relates to a medical device which has a plug fitted into the branch to form processing portions for performing several functions such as injection of medical fluids into the main tube (in this case, the processing portion is a mixing/injecting portion), sampling fluids from within the main tube (a fluid sampling portion) and monitoring the pressure in the main tube (a pressure monitoring portion), as exemplified by body fluid processing circuits, administration, blood sampling and blood transfusion sets, as well as administration, blood sampling and blood transfusion bags which are to be used either alone or in connection to those sets and circuits. The invention also relates to a process for producing such medical devices.

2. Description of the Related Art

The present invention will now be described in detail with particular reference to a body fluid processing circuit including a main tube made of a synthetic resin and which has branchline tubes and processing portions such as a mixing/injecting portion welded at several sites along its length, as well as to a process for producing the circuit.

As is well known, artificial kidneys, artificial lungs, plasma separators and other body fluid processors are equipped with body fluid processing circuits for connecting these apparatus to the human body. FIG. 36 shows an exemplary arterial blood circuit to be connected to an artificial kidney. As shown, the circuit includes a main tube 101 which usually has many branches provided along its length and they include a physiological saline filling line 102, a mixing/injecting portion 103 and a heparin line 104. Conventionally, the production of such branches has involved very cumbersome steps and required considerable skill.

A section of the mixing/injecting portion 103 is shown in FIG. 37. The conventional procedure of assembling this portion is shown in FIG. 38 and includes cutting the main tube 101 at a suitable site, applying a solvent 105 to the tips of the cut sections of the tube 101, pressing them into a connecting tube 107 with fingers, subsequently inserting a rubber plug 108 such as to close an opening 106 in the connecting tube 107 and fitting a cover 109 over the rubber plug 108.

This procedure is entirely manual and hence very cumbersome; in addition, controlling the coating weight of the solvent is difficult and requires considerable skill. If the solvent is applied in a more-than-necessary amount, the excess portion will come out of the joint, protrudes inward of the tube and solidifies to form lumps indicated by 110 in FIG. 37. The lumps 110 will increase the frictional resistance of blood flowing through the main tube, causing a turbulence in the blood which should form a laminar flow in a normal smooth conduit. This can be a cause of the disruption of blood components, which in turn may induce blood coagulation.

If the amount of the solvent is unduly small, not only is the main tube 101 joined to the connecting tube 107 insufficiently but also the resulting gap may potentially provide a passageway for the leakage of blood. In addition, the method of joining the two members by solvent application has a microbial contamination hazard or the solvent may dissolve in the blood to potentially cause adverse effects on the human body.

The following disadvantages and defects have been additionally pointed out to exist in the related art: (1) while the main tube 101 is molded by extrusion, the connecting tube 107 must separately be formed by injection and due to the different shrinkage ratios of the two molded parts, they cannot be joined together without producing steps in the joint; in addition, so many parts have to be assembled that the production cost increases and parts control is prone to be a cumbersome task; (2) the bore of the main tube 101 has to be adjusted to the exact dimension which fits to the connecting tube 107 and, in addition, it must be cut to the specified correct length; this only adds to the number of production steps and, hence, the manpower that is required; (3) due to the distortion introduced in the cut surfaces of the main tube 101, the latter will not fit closely to the connecting tube 107 and the applied solvent will adhere firmly to unwanted areas, thereby forming asperities which in turn cause blood coagulation and other troubles; (4) post-assembly sterilization will distort the joint between the main tube 101 and the connecting tube 107 and the distorted areas become accordingly smaller in diameter or steps may form to thereby upset the blood flow, which can be a cause of blood coagulation, residual blood or hemolysis.

For example, even a step about 0.1 mm (100 $\mu$m) high which is difficult to identify with the naked eye is an obstacle at least 10 times as large as erythrocytes which are the largest (8 $\mu$m is diameter) of the blood components; see FIG. 39 which shows enlarged encircled area A of FIG. 37. As a result, erythrocytes in the blood flowing through the main tube 101 to enter the connecting tube 107 impinge on the step and cannot move any farther. The erythrocytes gradually build up in areas around the step to become a cause of blood coagulation or residual blood and the disrupted erythrocytes resulting from the impingement will be a cause of hemolysis.

(5) The opening 106 in the connecting tube 107 is also wide enough to potentially cause the same problem as described in (4), i.e., blood may build up in areas about the step of the opening 106 to thereby cause clotting and residual blood.

(6) In the structure shown in FIG. 37 which has the main tube 101 connected to the connecting tube 107, the former is typically formed of a flexible synthetic resin and the latter of a rigid synthetic resin; hence, as shown in FIG. 40, the main tube 101 often kinks at sites near the connecting tube 107.

Under the circumstances, Japanese Patent Unexamined Publication No. 124249/1995 discloses a body fluid processing circuit having a main tube formed to have a straight surface without any seams present along its length, as well as a process for producing the circuit.

However, because of the absence of any holes in the main tube at the site where the mixing/injecting portion is formed, it is difficult to pierce a needle into the main tube. On the other hand, a small hole 121 (see FIG. 41) is formed in the mounting surface of the main tube 124; however, as is clear from FIG. 41, the small hole is formed with its outer peripheral surface protruding inward and when blood or other medical fluids contacted the protrusion 122, there is the possibility for the occurrence of stagnation, clotting, residual blood and other troubles.

SUMMARY OF THE INVENTION

The present invention has been accomplished on the basis of the intensive studies made by the inventors to eliminate the aforementioned disadvantages and defects of the prior art and its principal object is to provide a more improved method capable of efficient production of branches, such as the mixing injecting portion and the branchline, without the necessity of cutting the main tube and using solvents.

In one aspect, the present invention provides a process for producing a medical device having a branch, which includes the following steps: extruding a tubular form of a constituent material for a first tube under elevated temperature; welding a second tube firmly to the mounting surface of the first tube while aspirating the constituent material of the first tube from above the second tube; forming a hole in the mounting surface of the first tube by the aspiration such as to establish communication between the interior of the first tube and the interior of the second tube; and cutting the main first and assembling the medical device having branches.

In another aspect, the present invention provides a medical device having a branch, which includes: a first tube formed to have a straight surface without any seams present along its length; and a second tube welded firmly to the mounting surface of the first tube; with a hole being formed in the mounting surface of the first tube to establish communication with the second tube; and the outer peripheral surface of the hole being curved toward the mounting surface of the first tube.

DETAILED DESCRIPTION OF THE PREFERRED EMBODIMENTS

The present inventing will now be described in detail with particular reference to a body fluid processing circuit comprising a main tube made of a synthetic resin and which has branchline tubes and processing portions such as a mixing/injecting portion welded at several sites along its length, as well as to a process for producing the circuit.

Figure 1:
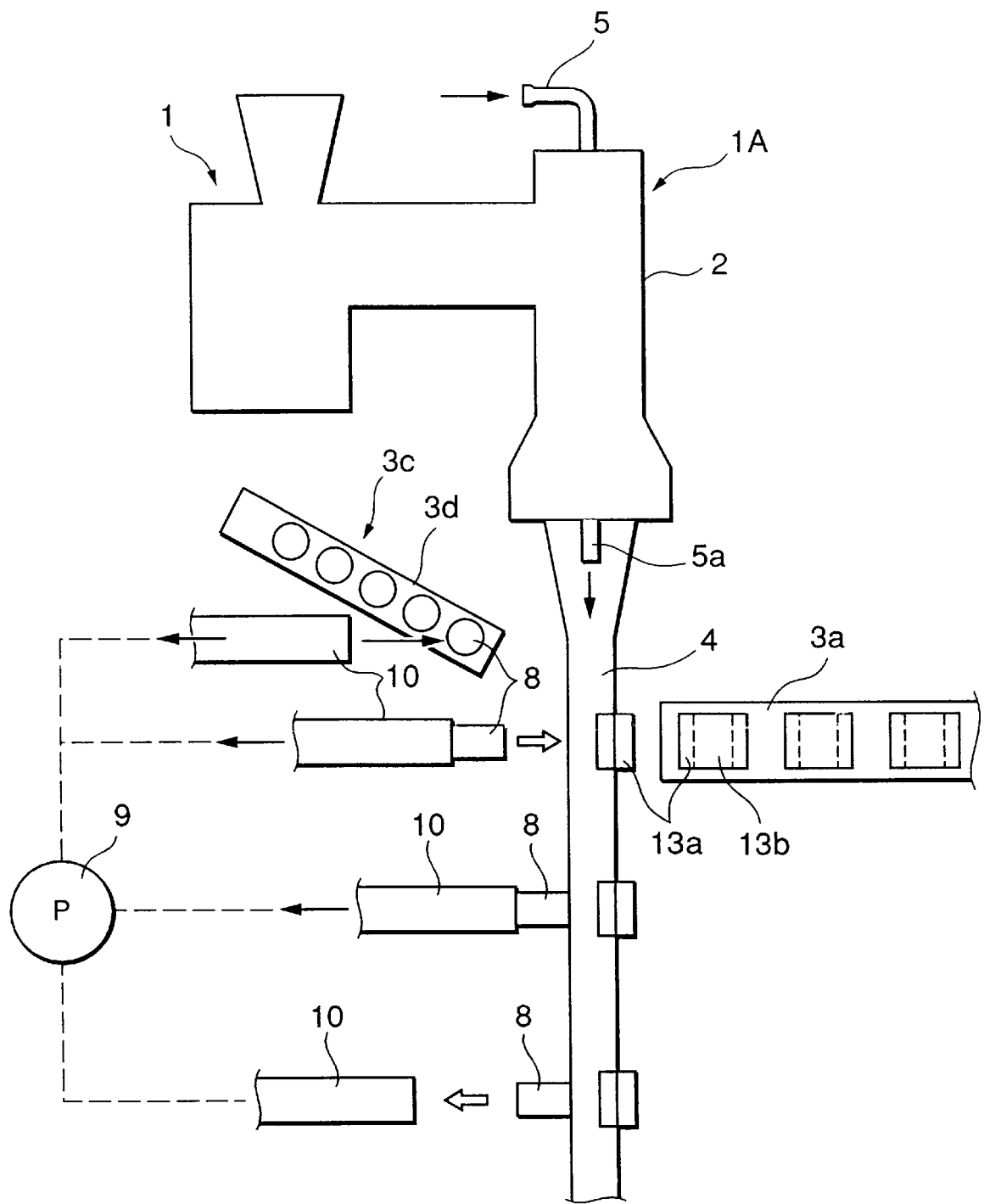
FIG. 1 is a schematic diagram illustrating an embodiment of the invention for producing a body fluid processing circuit.

FIG. 1 is a schematic diagram illustrating an embodiment of the invention for producing a body fluid processing circuit. Production equipment 1A is constructed by an extrusion molding machine 1, a mold 2 and an apparatus 3a for supplying a bottom member of a mixing/injecting portion. The mold 2 is fitted in the rear part with a line 5 for supplying sterile air and a nozzle 5a associated with the sterile air supply line 5 is provided to extend from the bottom of the mold 2. In the figure, numeral 10 is a suction pipe fitted with a tubular member 8 at the front end thereof and connected to a suction pump 9 in the rear end thereof. The tubular member 8 is made of a synthetic resin.

Numeral 4 is a thermoplastic synthetic resin of which the main tube is to be formed; the resin in molten form is extruded from the molding machine 1 into the mold 2, from which it emerges through the nozzle 5a to form a tube.

Figure 2:
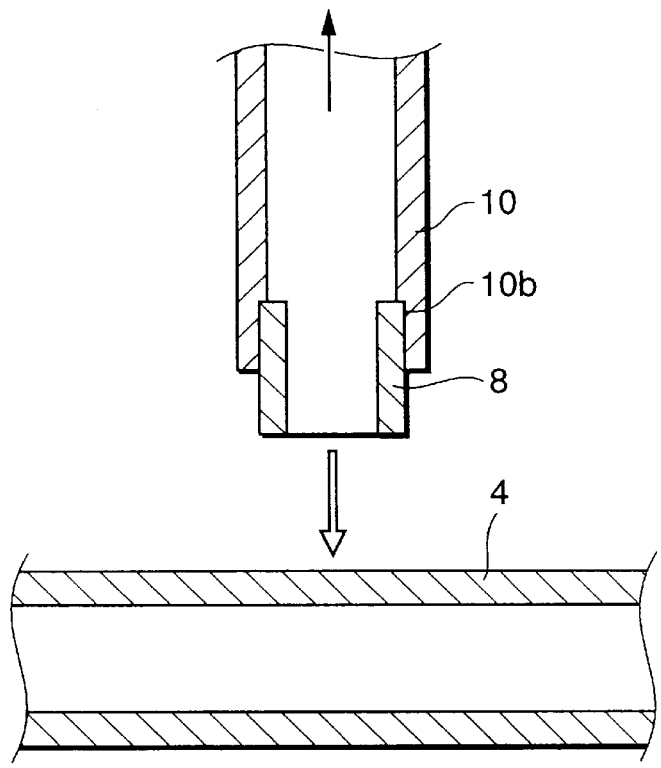
FIG. 2 is a partial enlarged view showing the first step of welding a tubular member to the main tube in the process shown in FIG. 1.
Figure 3:
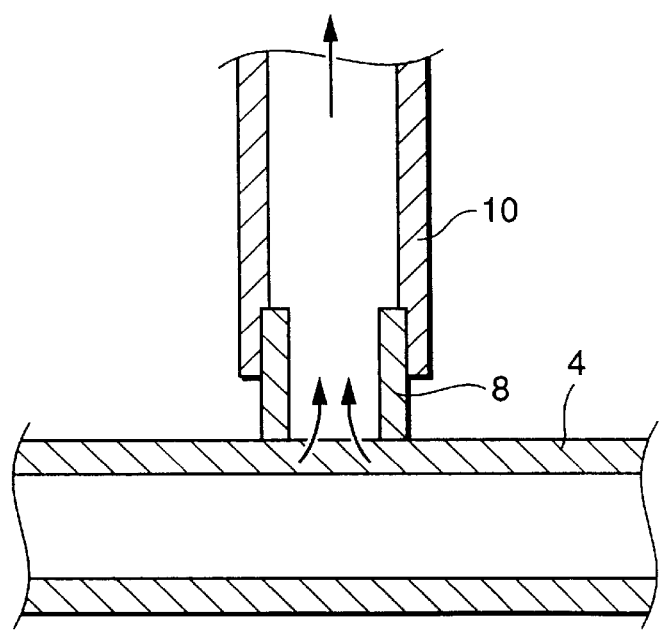
FIG. 3 is a partial enlarged view of the step subsequent to the step shown in FIG. 2.
Figure 4:
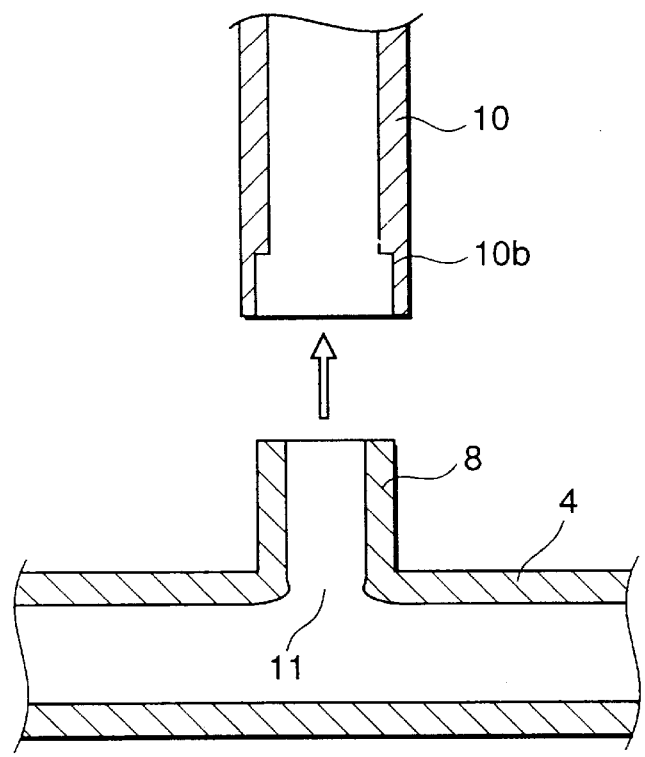
FIG. 4 is a partial enlarged view of the step subsequent to the step shown in FIG. 3.

Further referring to FIG. 1, a supplying apparatus 3a supplies and transports the bottom member 13a for the mixing/injecting portion 13 (to be described later and see FIG. 9) such that it is welded to a bottom surface of the tube 4, which is an opposite surface to the side where the mixing/injecting portion 13 is to be provided. The suction pipe 10 is driven back and forth (to the right and left in FIG. 1) and as shown in FIGS. 2 to 4, the bottom of the tubular member 8 is placed in contact with the mounting surface of the tube 4 and its constituent material is aspirated so that the tubular member 8 is welded firmly to the tube 4, with a hole 11 being formed in the mounting surface of the tube 4.

The step of welding the bottom member 13a to the bottom surface of the tube 4 may be performed at any time after the end of extrusion of the tube 4 and as long as the tube 4 is maintained at elevated temperature. For example, the bottom member 13a may be welded to the tube 4 simultaneously with the welding of the tubular member 8. Alternatively, the bottom member 13a may be welded to the tube 4 before or after the welding of the tubular member 8.

In order to ensure positive welding to the tube 4, the bottom of the tubular member 8 and a groove 13b on the bottom member 13a of the mixing/injecting portion 13 (at which the bottom member 13a contacts the bottom surface of the tube 4 which is opposite to its mounting surface where the mixing/injecting portion 13 is to be provided) may be heated before they are welded to the tube 4.

For example, the tubular member 8 may be supplied by a feed device 3c (having a hot plate 3d for transporting the tubular member 8 toward the extruded tube 4) such that the bottom of the tubular member 8 carried on the hot plate 3d is heated with the hot plate 3d and maintained at elevated temperature while the top of the tubular member 8 is fitted on the suction pipe 10 so as to weld the bottom of the tubular member 8 to the mounting surface of the extruded tube 4 in the manner described above.

In addition, a heating device (not shown) may be provided above the bottom member 13a so that the groove 13b on the bottom member 13a is heated and maintained at elevated temperature while the bottom member 13a is welded to the bottom surface of the extruded tube 4.

If desired, the feed apparatus 3a may be constructed by a hot plate so that the groove 13b on the bottom member 13a is placed in contact with the apparatus 3a and kept at elevated temperature while the bottom member 13a is welded to the bottom surface of the extruded tube 4.

The unit for heating the surfaces of the tubular member 8 and the bottom member 13a which are to be welded to the tube 4 is by no means limited to those described above and any other techniques may be employed as long as the intended result is attained.

The tube 4 is formed by using sterile air being supplied through the feed line 5, so it can be maintained in an inflated state. Further, the tube 4 being extruded is kept in a closed system while the tubular member 8 is fitted on the tube 4 and, hence, a clean operation can be realized in the absence of any dust and other foreign matter that may otherwise be deposited in the interior of the tube 4.

FIG. 2 is an enlarged view showing the first step of welding the tubular member 8 to the tube 4 being extruded from the mold 2. With the tubular member 8 kept on groove 10b on its inner circumference by suction, the suction pipe 10 is moved toward the mounting surface of the tube 4 and the bottom of the tubular member 8 is brought into intimate contact with the mounting surface of the tube 4 as shown in FIG. 3.

The constituent material of the tube 4 in areas around the bottom of the tubular member 8 is pulled toward the latter so that the tube 4 is firmly welded to the tubular member 8. The constituent material of the tube 4 in contact with the bottom of the tubular member 8 further passes through the bore of the tubular member 8 so as to be sucked into the suction pipe 10. As a result, a hole 11 is formed as shown in FIG. 4 and, at the same time, the tubular member is welded to become an integral part of the mounting surface of the tube 4. The outer peripheral surface of the hole 11 thus formed in the wall of the tube 11 is slightly curved upward as shown in FIG. 4 and two primary factors involved in this phenomenon are as follows: i) the suction provided by the suction pipe 10 during the formation of the hole 11, and ii) the reaction to the movement of the tubular member 8 away from the tube 4 in order to disconnect it from suction pipe 10 after the end of the aspiration.

If desired, aspiration may only be performed in the step of welding the bottom of the tubular member 8 to the mounting surface of the tube 4 and forming the hole 11. In this case, the tubular member 8 is not aspirated as in FIG. 2 but is placed in light engagement with the groove 10b to prevent the tubular member from coming off; thereafter, suction is applied to weld the bottom of the tubular member 8 the mounting surface of the tube 4 firmly and form the hole 11 in it; subsequently, the suction is removed and the suction pipe 10 is moved away from the tube 4 to be disengaged from the tubular member 8.

Figure 5:
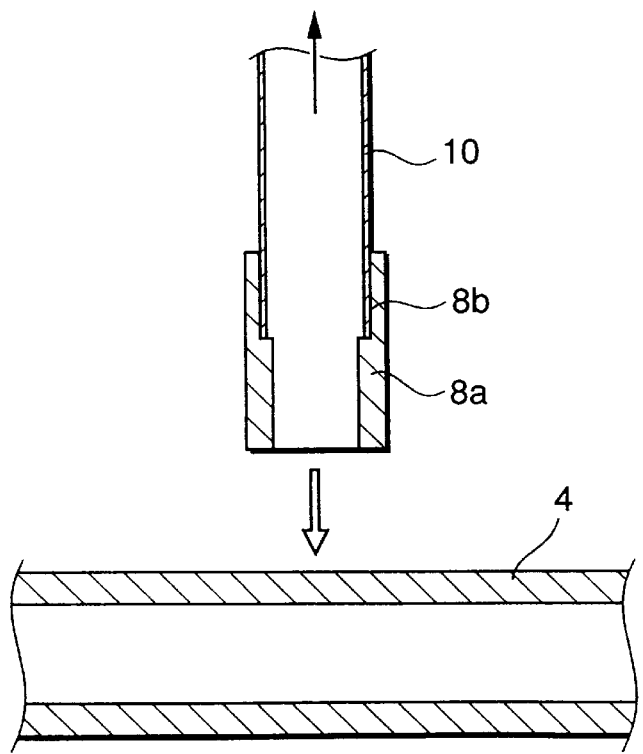
FIG. 5 is a schematic diagram illustrating a step in another exemplary process for producing the body fluid processing circuit of the invention.
Figure 6:
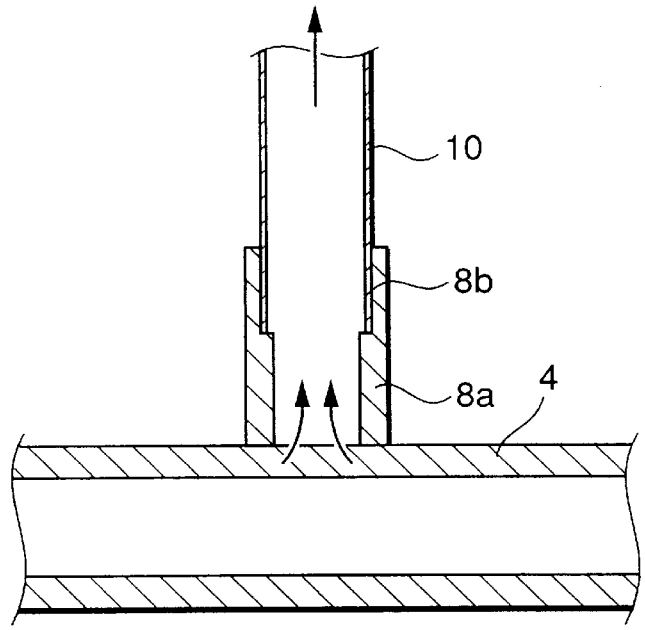
FIG. 6 is a schematic diagram showing the step subsequent to the step shown in FIG. 5.
Figure 7:
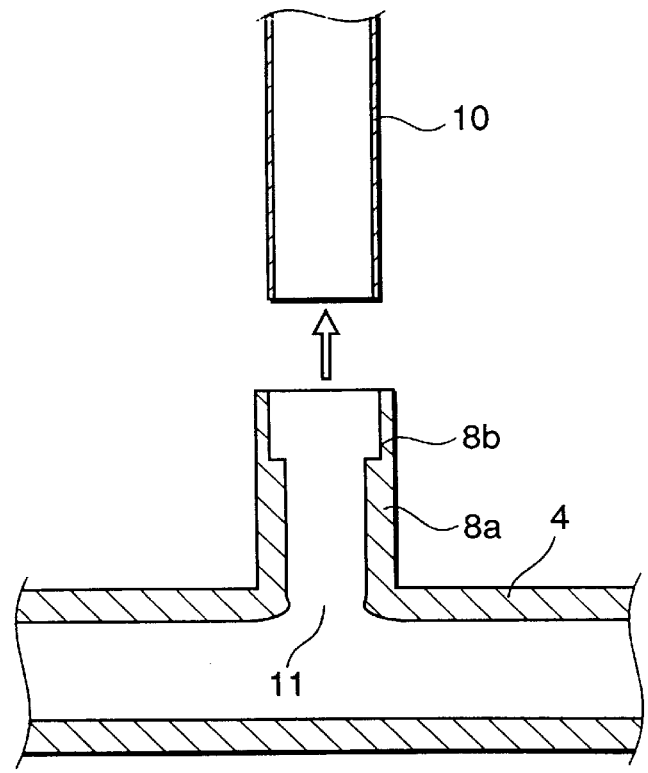
FIG. 7 is a schematic diagram showing the step subsequent to the step shown in FIG. 6.

The tubular member 8 may be replaced by one of a different shape which, as indicated by 8a in FIG. 5, has a groove 8b formed on the inner surface. With suction being applied, the tip of the suction pipe 10 is placed in engagement with the groove 8b and the procedure described by reference to FIGS. 2 to 4 is repeated to weld the tubular member 8a to become an integral part of the mounting surface of the tube 4 and form the hole 11 as shown in FIGS. 5 to 7.

Figure 8:
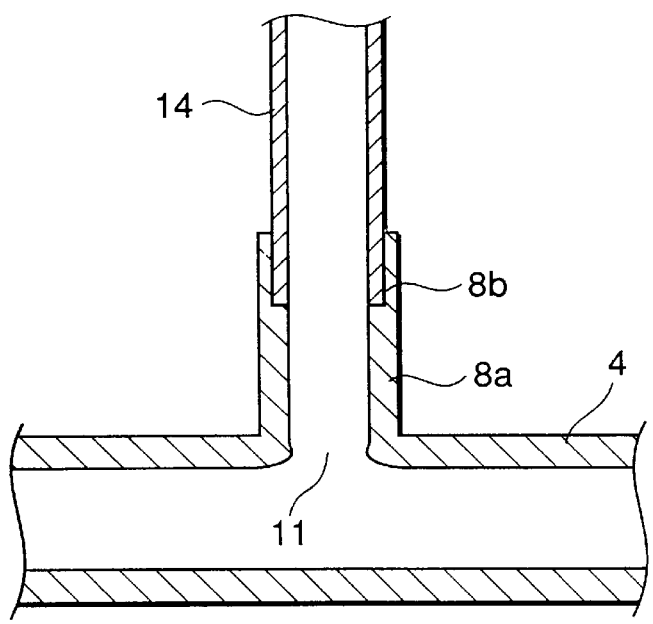
FIG. 8 shows enlarged a tubular member 8a to which a branchline tube 14 is connected to provide a flush surface.

The tubular member 8a has the advantage that when the branchline tube 14 is connected to the groove 8b as shown in FIG. 8, any steps that would otherwise form in the fluid passageway can be eliminated.

Figure 9:
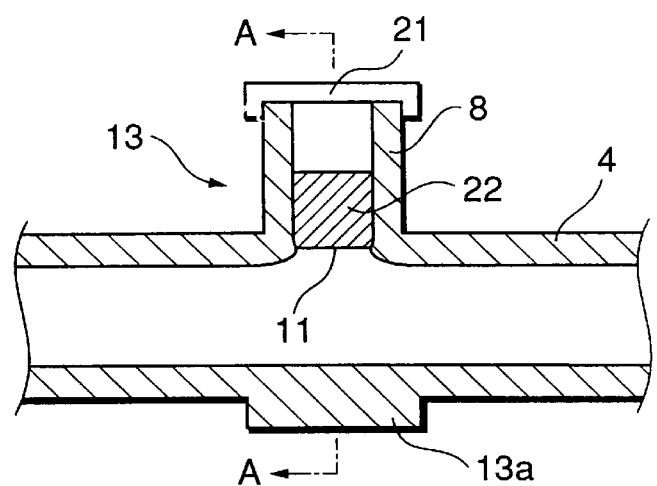
FIG. 9 is a schematic diagram showing how a mixing/injecting portion is assembled by pressing a rubber plug into a tubular member 8.
Figure 10:
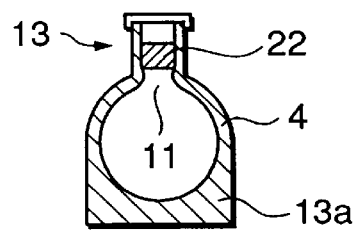
FIG. 10 is section A—A of FIG. 9.

With respect to forming the mixing/injecting portion 13, a plug 22 such as a rubber plug is pressed into the tubular member 8 and a cap 21 is fitted on its top as shown in FIG. 9 (section A—A of which is shown in FIG. 10). The outer peripheral surface of the hole 11 in the tube 4 is slightly curved toward the top of the tubular member 8 so that the lower end of the plug 22 will not protrude from the lower edge of the hole 11.

The bottom member 13a fitted on the bottom surface of the tube 4 which is remote form the tubular member 8 on the mounting surface of the tube 4 has the advantage of ensuring safety during use since there is no possibility for a needle piercing through the stopper 22 to penetrate the other side of the tube 4 to injure the operator.

Figure 11:
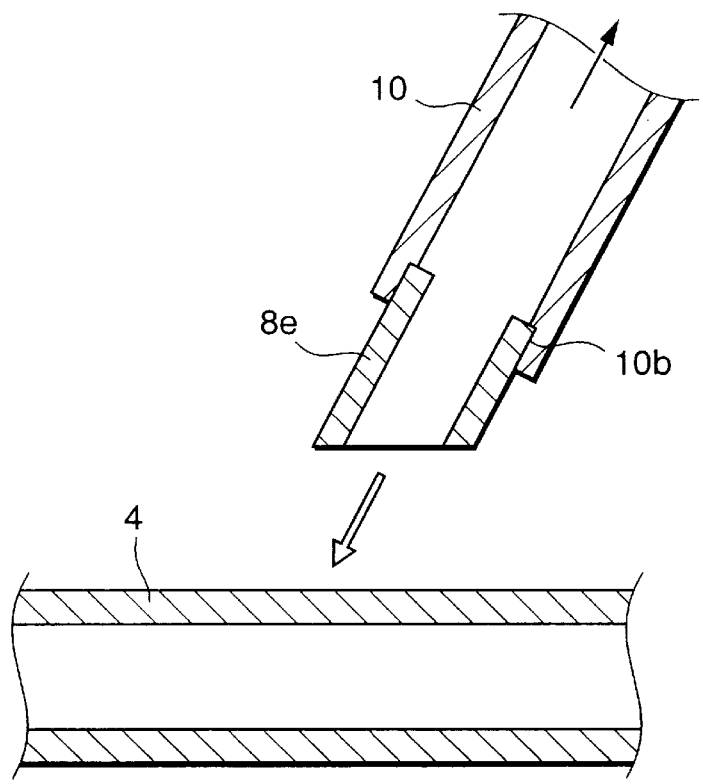
FIG. 11 is a partial enlarged view showing a step in yet another exemplary process for producing the body fluid processing circuit of the invention.
Figure 12:
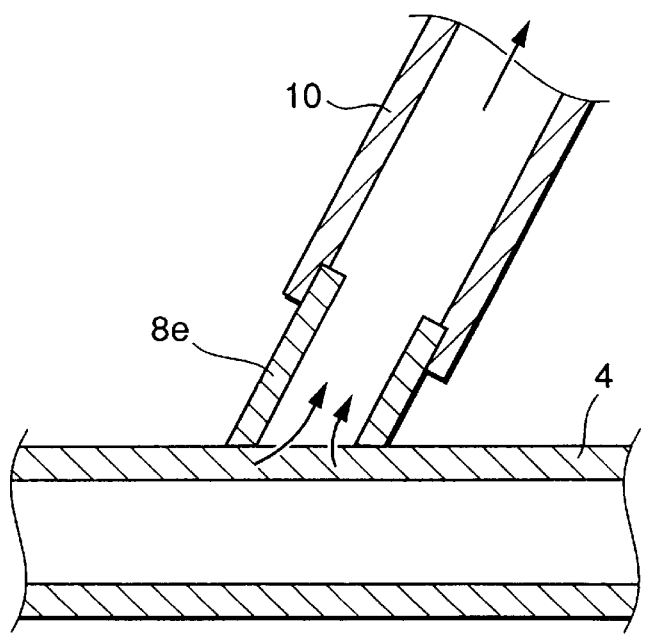
FIG. 12 is a partial enlarged view showing the step subsequent to the step shown in FIG. 11.
Figure 13:
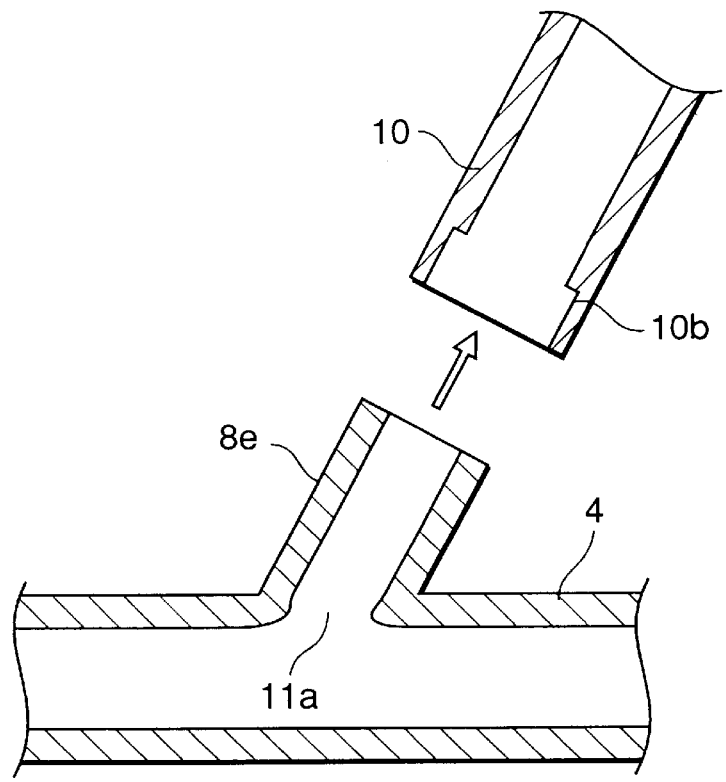
FIG. 13 is a partial enlarged view showing the step subsequent to the step shown in FIG. 12.

In the embodiments described above, the tubular member 8 or 8a is welded at right angles to the tube 4. In another embodiment of the invention, a tubular member 8e may be welded at an angle to the tube 4 as shown in FIGS. 11 to 13. To do this, the tubular member 8e cut at an angle at the tip is placed in engagement with the groove 10b in the suction pipe 10 under suction or, alternatively, the tubular member 8 is placed in light engagement with the groove 10b in the absence of suction; subsequently, the suction pipe 10 is moved obliquely downward so that the bottom of the tubular member 8e contacts the mounting surface of the tube 4 and its constituent material is separated to have the bottom of the tubular member 8e welded firmly to the tube 4 while forming a hole 11a in the mounting surface of the tube 4 (see the sequence of steps shown in FIGS. 11 to 13). Again, the outer peripheral surface of the hole 11a may be curved slightly upward as in the case of the hole 11.

Figure 14:
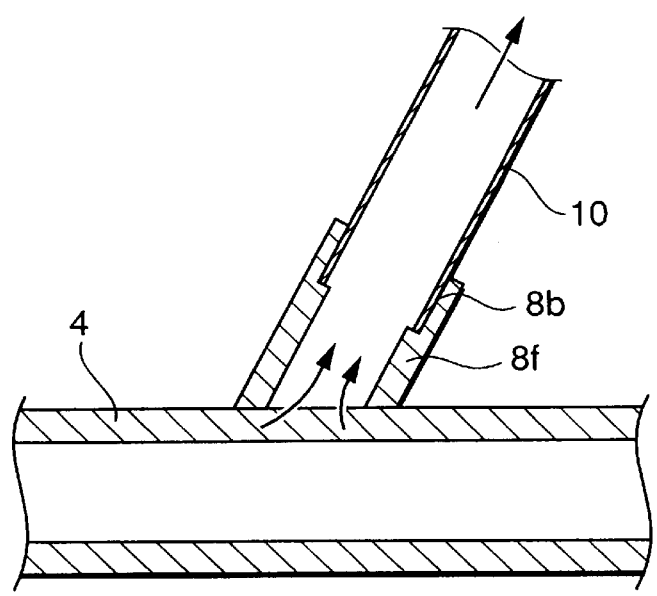
FIG. 14 is a partial enlarged view showing a modification of the step shown in FIG. 12.
Figure 15:
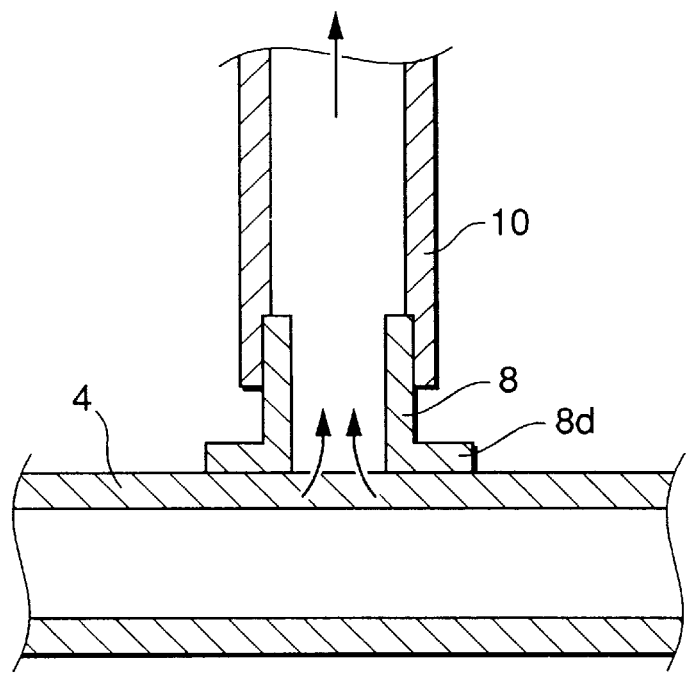
FIG. 15 is a partial enlarged view showing a step in a further exemplary method of producing the body fluid processing circuit of the invention.
Figure 16:
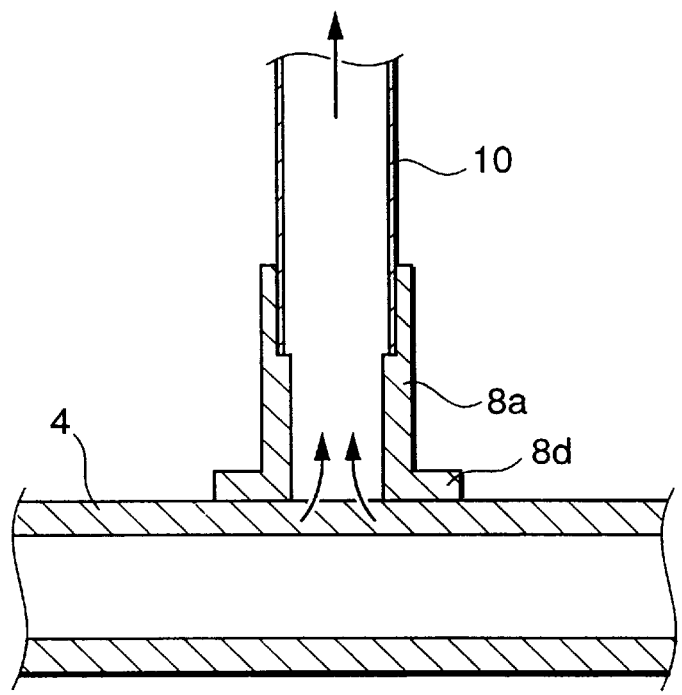
FIG. 16 is a partial enlarged view showing a step in another exemplary method of producing the body fluid processing circuit of the invention.
Figure 17:
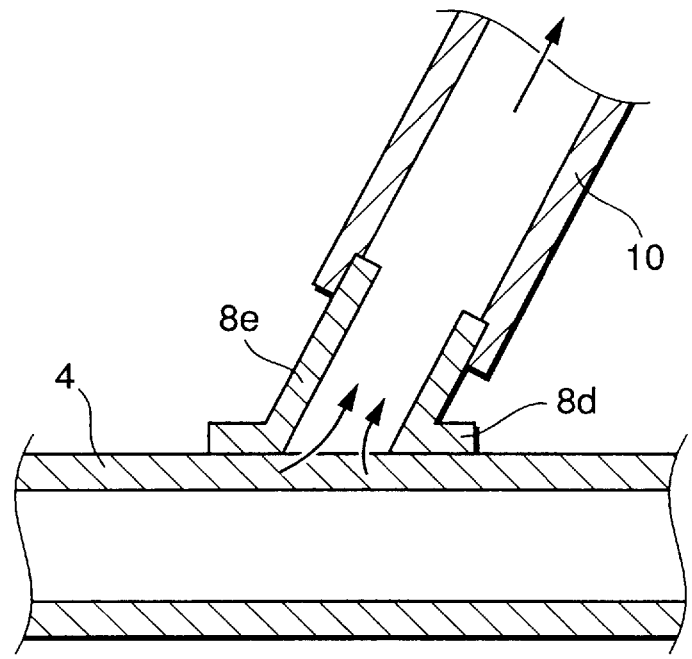
FIG. 17 is a partial enlarged view showing a modification of the step shown in FIG. 15.
Figure 18:
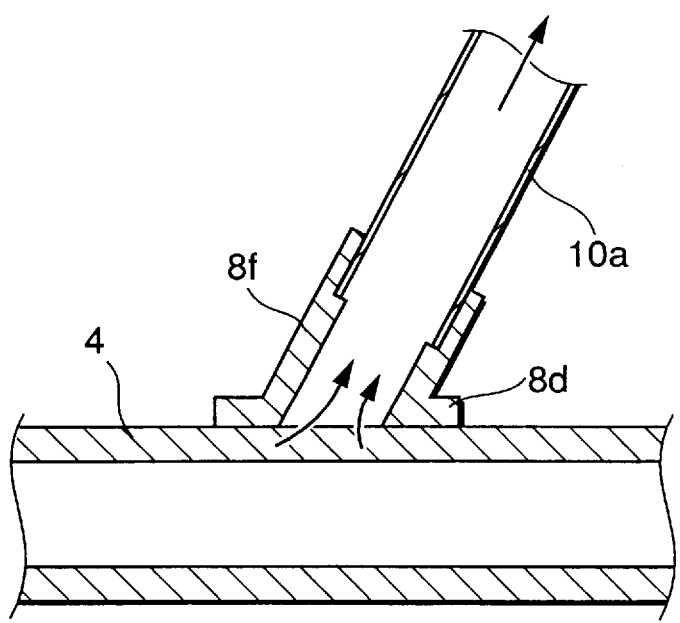
FIG. 18 is a partial enlarged view showing a modification of the step shown in FIG. 16.

FIG. 14 shows a modification of the method illustrated in FIGS. 11 to 13 and a tubular member indicated by numeral 8f can also be welded to the mounting surface of the tube 4, with a hole 11a being formed in it.

As in the case of the tubular member 8a, a branchline tube 14 can be connected to the tubular member 8f. In addition, as in the case of the tubular member 8, a plug 22 may be pressed into the tubular member 8e shown in FIG. 13 with a cap 21 being fitted over the top to form a mixing/injecting portion 13. In this case, a bottom member 13a may also be fitted on the bottom surface of the tube 4 which is an opposite side to the tubular member 8e on the mounting surface of the tube 4.

The curvature and profile of the outer peripheral surface of the hole 11 or 11a in the wall of the tube 4 can be freely adjusted by controlling various factors including the force of suction created by the suction pipe 10, the timing at which the suction is removed after forming the hole 11 or 11a, and the speed at which the suction pipe 10 is moved away from the tube 4. Preferably, the outer peripheral surface of the hole is slightly curved toward the mounting surface of the tube 4 as shown in FIG. 13. This is because the branchline tube 14 can be connected to the tubular member 8 without forming any steps in the fluid passageway (see FIG. 8) and there is no obstacle to the passage of a fluid through the tube 4.

In the present invention, the bottom surface of the tubular member 8 (or 8a, 8e or 8f) is welded to the tube 4 with suction being applied and this ensures firm and consistent welding of the bottom surface of the tubular member 8 (or 8a, 8e or 8f) to the mounting surface of the tube 4 without taking the trouble of providing a flange at the bottom of the tubular member. However, if desired, as shown in FIGS. 15 to 18, a flange 8d may be provided at the bottom of the tubular member (or 8a, 8e or 8f) to assist in the welding of the tubular member to the mounting surface of the tube 4 so as to become an integral part of it while forming a hole 11a or 11a in the surface.

Figure 19:
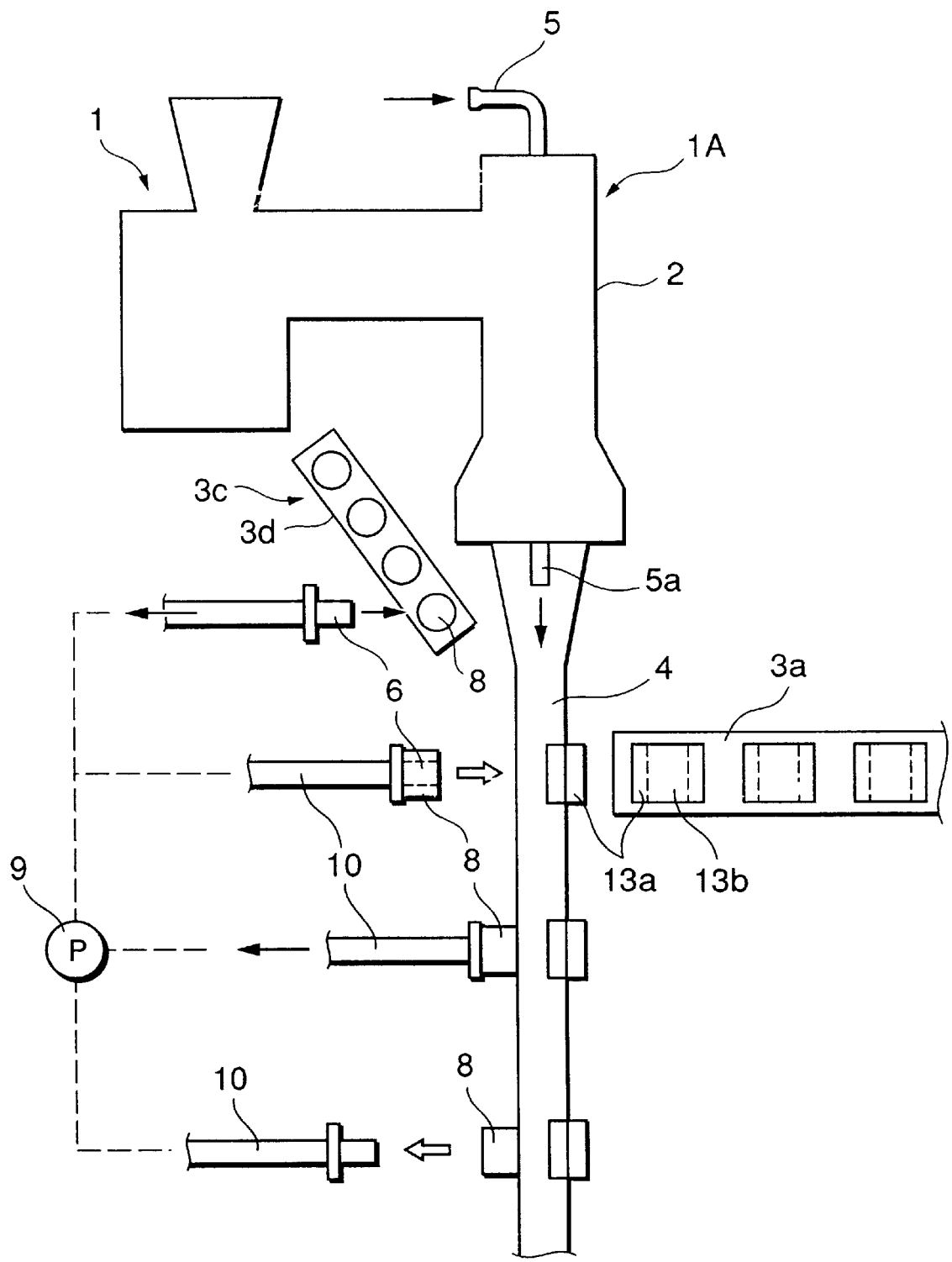
FIG. 19 is a schematic diagram illustrating another embodiment of the invention for producing a body fluid processing circuit.

FIG. 19 is a schematic diagram illustrating another embodiment of the invention for producing a body fluid processing circuit. Numeral 6 is a jig having a suction port 7 (see FIG. 20) around which a tubular member 8 is fitted and the rear end of which is connected to a suction pipe 10 which, in turn, is connected to a suction pump 9. The jig 6 moves back and forth (to the right and left in FIG. 19) and, as shown in FIGS. 20 to 22, the bottom of the tubular member 8 is welded to the tube 4 while, at the same time, the tip of the suction port 7 is placed in contact with the mounting surface of the tube 4 (or pierced into or through the mounting surface) so that the constituent material of that mounting surface is aspirated, thereby permitting the tubular member 8 to be firmly welded to the tube 4 with a hole 11 being formed in its mounting surface.

Figure 20:
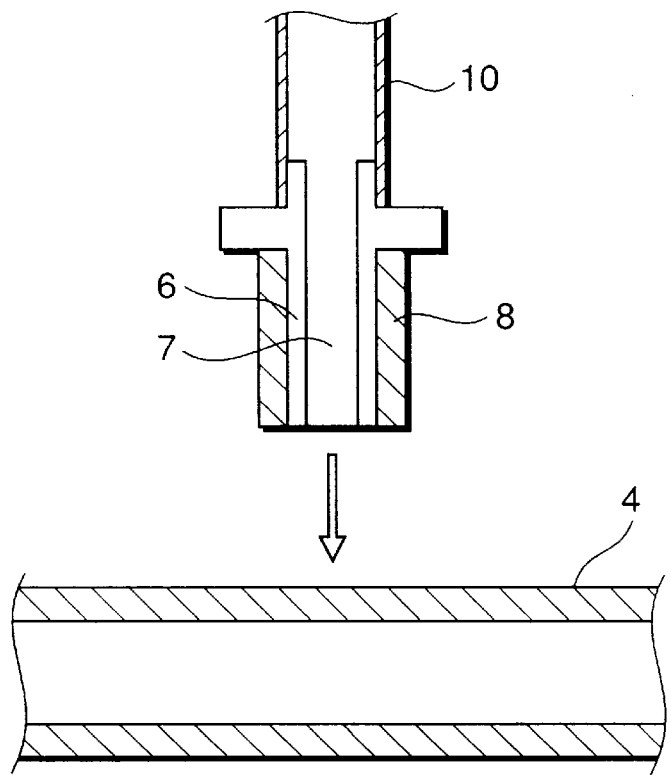
FIG. 20 is a partial enlarged view showing a step in yet another exemplary method of producing the body fluid processing circuit of the invention.

FIG. 20 is an enlarged view showing the first step of welding the tubular member 8 to the tube 4 being extruded from the mold 2. The jig 6 around which the tubular member 8 is fitted and which has a flat tip is moved toward the mounting surface of the tube 4 and, as shown in FIG. 21, the tip of the jig 6 is placed in contact with the mounting surface of the tube 4 and, at the same time, the bottom surface of the tubular member 8 is brought into intimate contact with the mounting surface.

When air is drawn through the suction port 7, the constituent material of the tube 4 located around the tip of the suction port 7 is attracted toward the tubular member 8, whereby the tubular member 8 is firmly welded to the tube 4. Further, the constituent material of the tube 4 which is in contact with the tip of the suction port 7 is drawn into the latter, whereupon a hole 11 is formed and the tubular member 8 is welded to the mounting surface of the tube 4 to become an integral part of it. The outer peripheral surface of the hole 11 in the tube 4 is curved slightly upward under the action of two forces, one being the suction through the suction port 7 and the other being the reaction to the movement of the suction port 7 away from the tube 4 after the suction is removed following the formation of the hole 11 (see FIG. 22).

Figure 21:
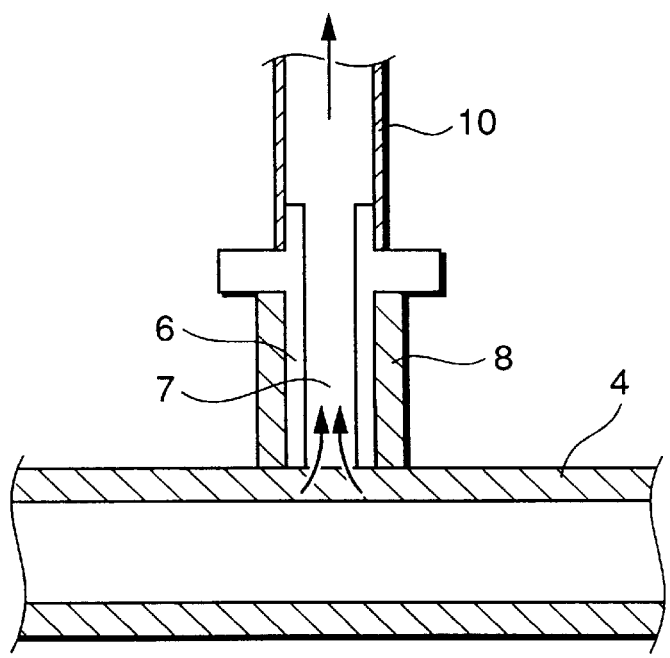
FIG. 21 is a partial enlarged view showing the step subsequent to the step shown in FIG. 20.
Figure 22:
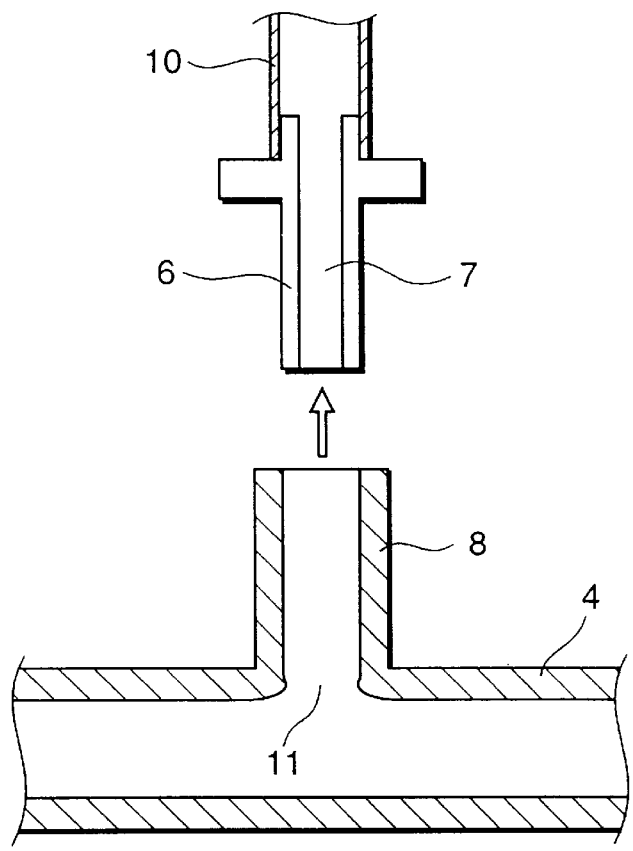
FIG. 22 is a partial enlarged view showing the step subsequent to the step shown in FIG. 21.
Figure 23:
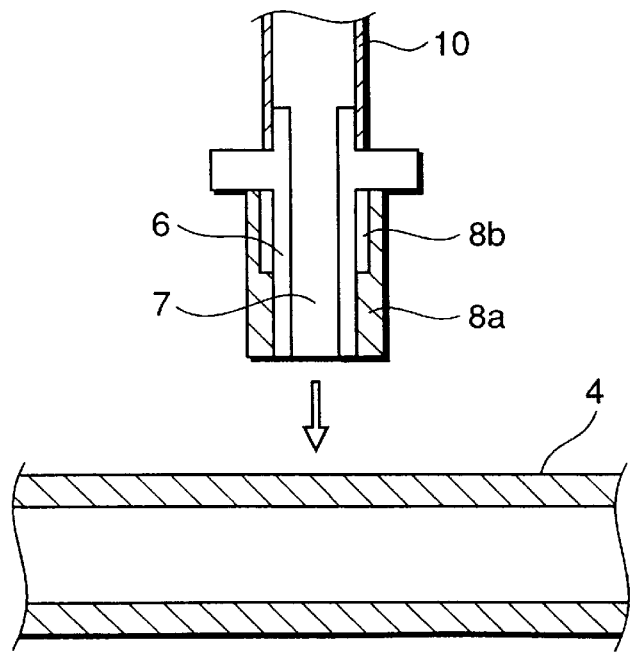
FIG. 23 is a partial enlarged view showing a modification of the step shown in FIG. 20.

If desired, a tubular member 8a having an internal groove 8b may be fitted around the jig 6 as shown in FIG. 23 and worked as in the process shown in FIGS. 20 to 22 so that the tubular member 8a is welded to the mounting surface of the tube 4 to become an integral part of the latter while forming a hole 11 in the mounting surface.

Figure 24:
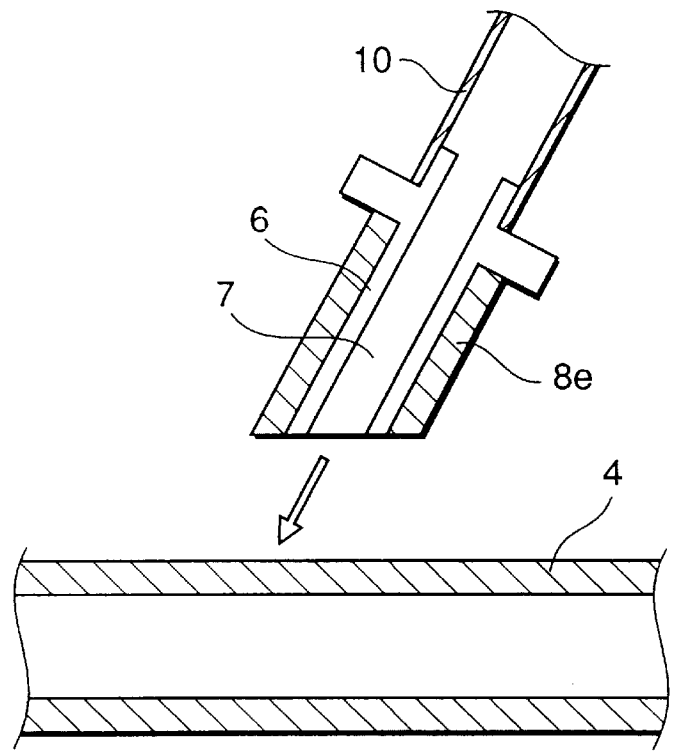
FIG. 24 is a partial enlarged view showing a step in a further exemplary method of producing the body fluid processing circuit of the invention.
Figure 25:
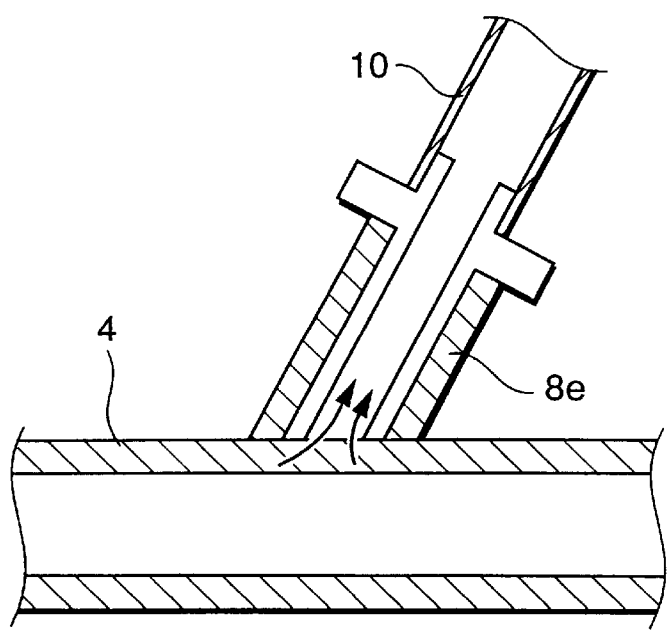
FIG. 25 is a partial enlarged view showing the step subsequent to the step shown in FIG. 24.
Figure 26:
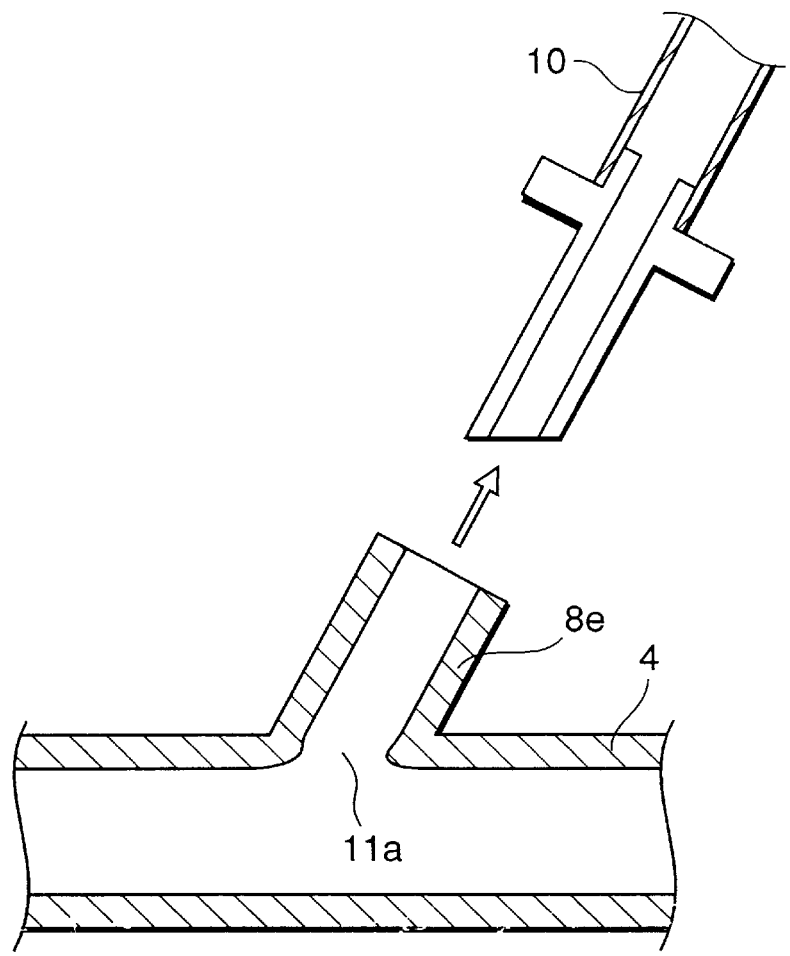
FIG. 26 is a partial enlarged view showing the step subsequent to the step shown in FIG. 25.

In the foregoing description, the tubular member 8 (or 8a) fitted around the jig 6 is welded at right angles to the tube 4. This is not always the case of the invention and as shown in FIGS. 24 to 26, a tubular member 8e may be welded at an angle to the tube 4. For example, the tubular member 8e cut at an angle at the tip is fitted around the jig 6 also cut at an angle at an end and the jig is driven obliquely downward so that the bottom surface of the tubular member 8e is welded to the tube 4 and, at the same time, the tip of the suction port 7 is placed in contact with the mounting surface of the tube 4 and its constituent material is aspirated to form the hole 11a in the mounting surface (see FIGS. 24 to 26). Again, the outer peripheral surface of the hole 11a may be curved slightly upward as in the case of the hole 11.

The profile of the outer peripheral surface of the hole 11 or 11a in the tube 4 can be adjusted freely by controlling various factors including the suction through the suction port 7, the depth to which the suction port 7 is pierced into the mounting surface of the tube 4 (in case that the sharp-pointed suction port 7 may be pierced halfway the thickness of the wall or pierced through it completely), or the speed at which the suction port 7 is moved away from the tube 4 after removing the suction.

Figure 27:
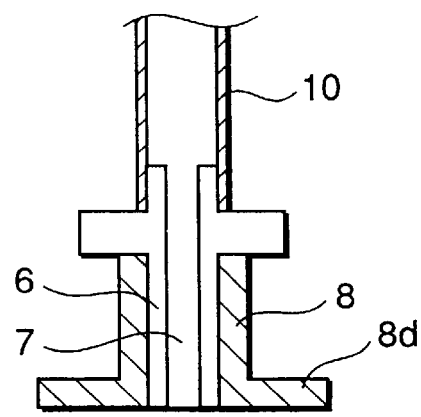
FIG. 27 is a partial enlarged view showing a step in another exemplary method of producing the body fluid processing circuit of the invention.
Figure 28:
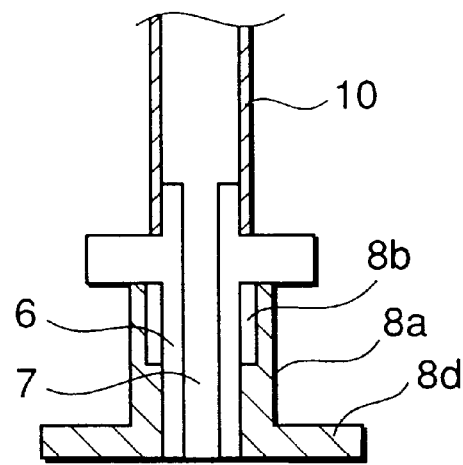
FIG. 28 is a partial enlarged view showing a modification of the step shown in FIG. 27.
Figure 29:
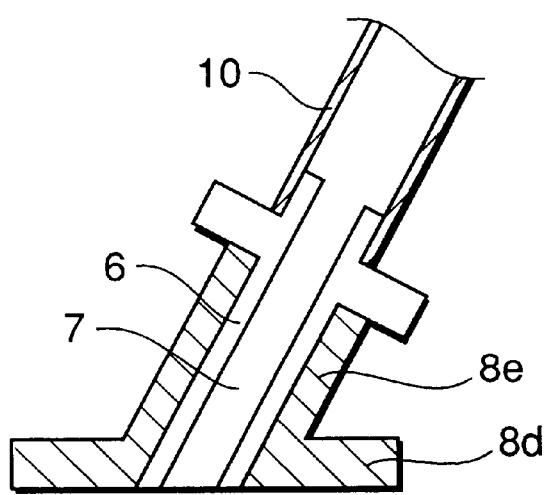
FIG. 29 is a partial enlarged view showing a modification of the step shown in FIG. 27.

In the embodiment just described above, the bottom surface of the tubular surface 8 (or 8a or 8e) is welded to the tube 4 with suction being applied and this ensures firm welding of the bottom surface of the tubular member 8 (or 8a or 8e) to the mounting surface of the tube 4 without taking the trouble of providing a flange at the bottom of the tubular member. However, if desired, as shown in FIGS. 27 to 29, a flange 8d may be provided at the bottom of the tubular member 8 (or 8a or 8e) to assist in the welding of the tubular member to the mounting surface of the tube 4 to become an integral part of it while forming a hole 11 or 11a in the surface.

Figure 30:
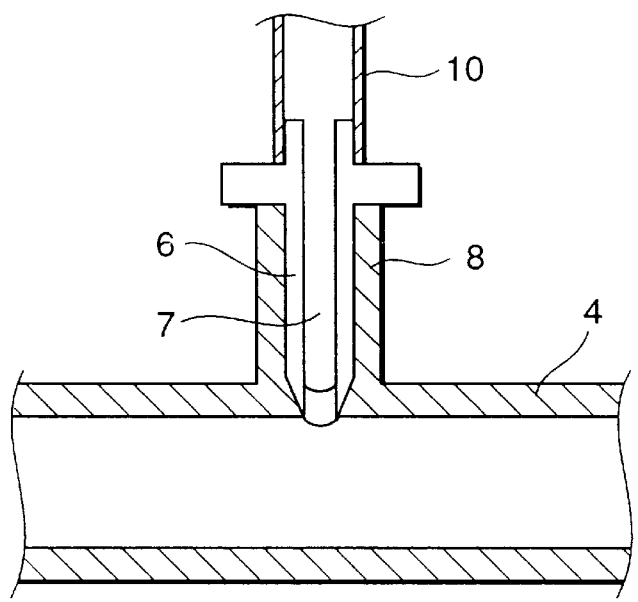
FIG. 30 is a partial enlarged view showing a step in a further exemplary method of producing the body fluid processing circuit of the invention.
Figure 31:
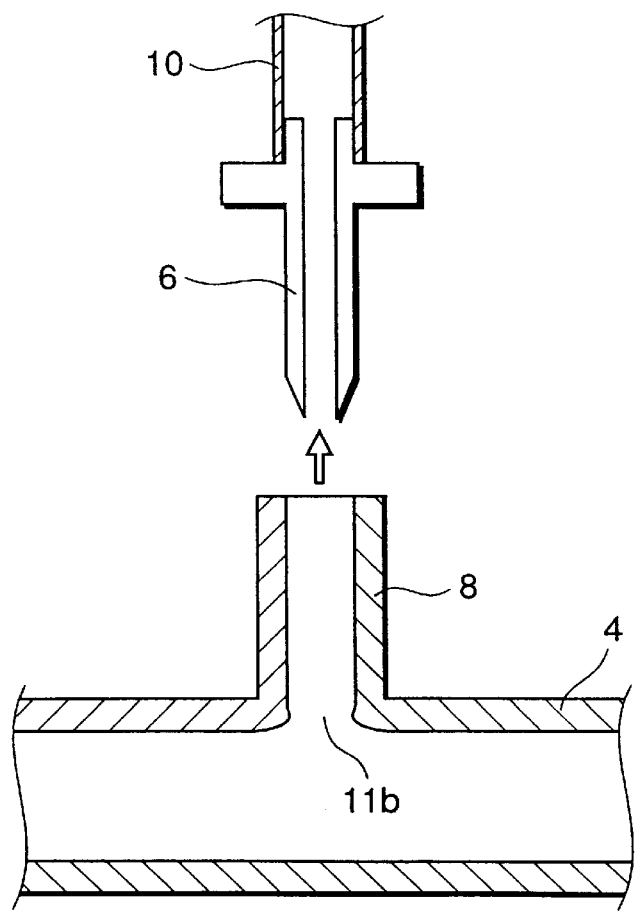
FIG. 31 is a partial enlarged view showing the step subsequent to the step shown in FIG. 30.
Figure 32:
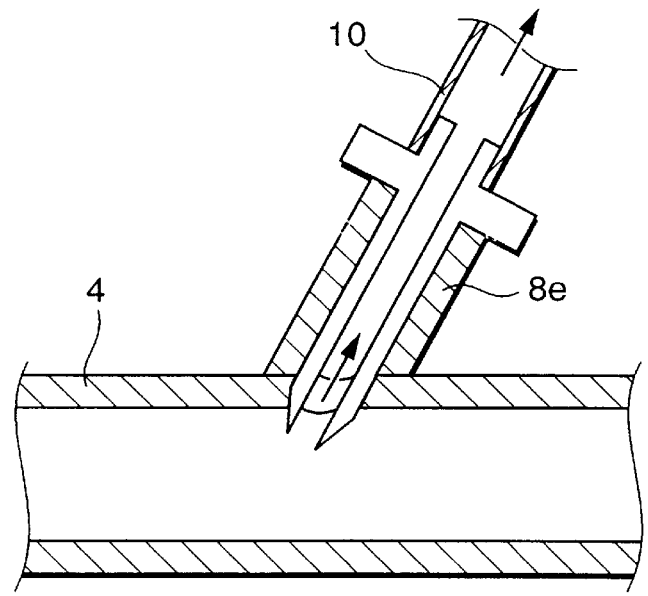
FIG. 32 is a partial enlarged view showing a step in another exemplary method of producing the body fluid processing circuit of the invention.
Figure 33:
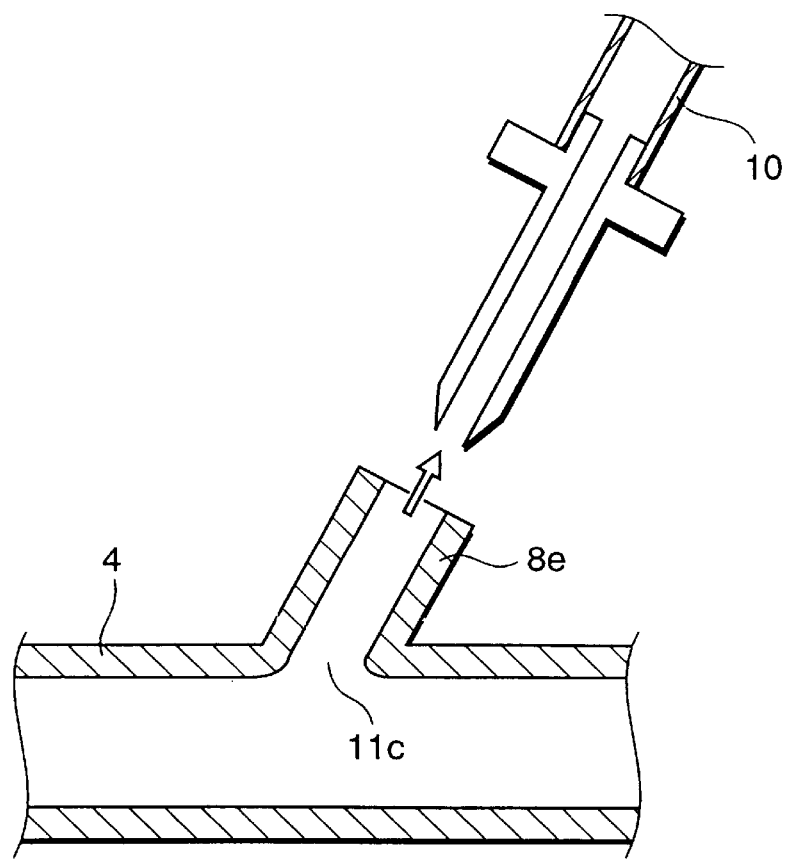
FIG. 33 is a partial enlarged view showing the step subsequent to the step shown in FIG. 32.
Figure 34:
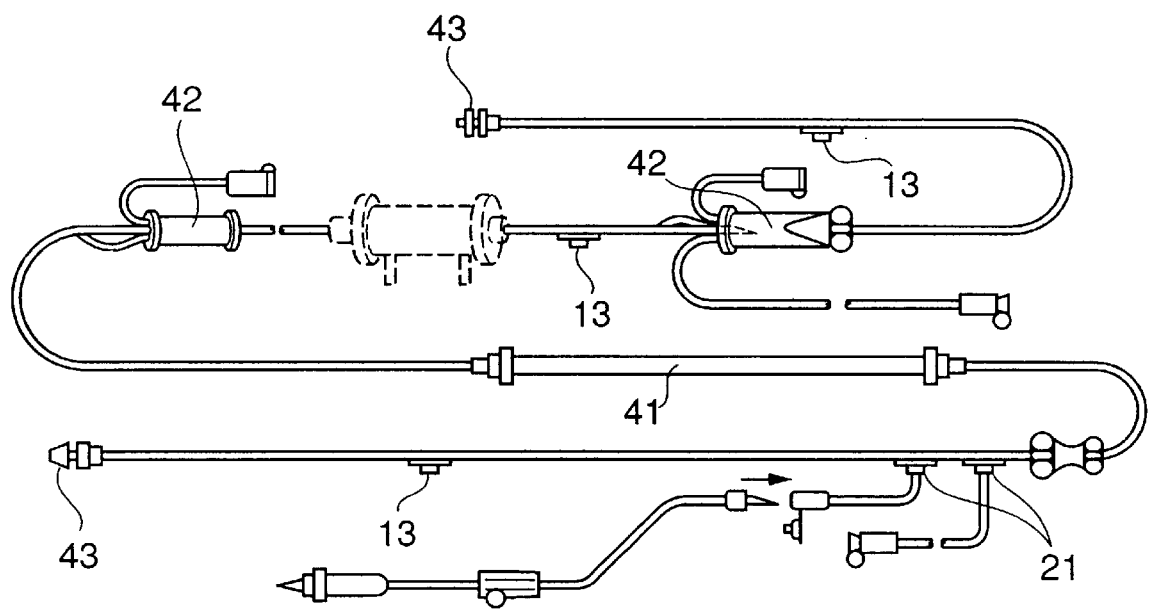
FIG. 34 is a schematic diagram of the body fluid processing circuit of the invention.

In the processes shown in FIGS. 20 to 22 and in FIGS. 24 to 26, the tip of the suction port 7 of the jig 6 is kept in contact with the mounting surface of the tube 4 while its constituent material is aspirated to form the hole 11 or 11a. If desired, the suction port 7 of the jig 6 may be cut to have a sharp-pointed end and pierced into the mounting surface of the tube 4 as shown in FIG. 30 or completely pierced through the surface as shown in FIG. 32 and the constituent material of the tube 4 is aspirated to form a hole which is indicated by 11b in FIG. 31 or 11c in FIG. 33. As already noted with reference to FIGS. 2 to 4, the outer peripheral surface of the hole 11b or 11c may be curved slightly upward.

After welding the tubular member 8 (or 8a, 8e or 8f) to the mounting surface of the tube 4 and forming the hole 11 or 11a in it, the branchline 14 is connected to the tubular member and/or the plug 22 is pressed into the tubular member and given the necessary work to construct the mixing/injecting portion (processing portion) 13 and the tube 4 is cut to a specified length; thereafter, a rolling tube 41, a drip chamber 42, a shunt adapter 43 and any other components of a medical device such as a container in bag form or a needle are connected-to the tube to assemble a body fluid processing circuit (a medical device having branches). Alternatively, the body fluid processing circuit (the medical device having branches) is first assembled by connecting the necessary components of the medical device and thereafter the branchline tube 14 is connected to the tubular member 8 (or 8a, 8e or 8f) and further the mixing/injecting portion (processing portion) 13 may be constructed.

As described on the foregoing pages, the jig 6 may be fitted on top of the tubular member 8 (or 8a, 8e or 8f) so that its bottom is welded to the mounting surface of the tube 4 to become an integral part of the latter; alternatively, the jig 6 is dispensed with and the suction pipe 10 is directly connected to the top of the tubular member 8 (or 8a, 8e or 8f) and suction is applied to ensure that the bottom of the tubular member is firmly welded to the mounting surface of the tube 4; in either case, the hole 11 (or 11a, 11b or 11c) can be formed in the mounting surface of the tube 4 so that the interior of the tubular member 8 (or 8a, 8e or 8f) communicates with the interior of the tube 4.

The concept of the invention is applicable not only to the body fluid processing circuit described above in detail but also to all kinds of medical devices having branches that are mentioned in the Background of the Invention, as exemplified by body fluid processing circuits, administration, blood sampling-and blood transfusion bags which are to be used either alone or in connection to those sets and circuits. Hence, it should be understood that the scope of the invention encompasses all kinds of medical devices having branches.

In the invention, the main tube 4 and the tubular member 8 (or 8a, 8e or 8f) may assume any cross-sectional shape such as a circle, ellipsis, square or a rectangle. If the tube 4 in a circular or elliptical form is to be welded to the tubular member which is also circular or elliptical, the welding operation may be facilitated by forming a groove in the bottom of the tubular member 8 (8a, 8e or 8f) or the flange 8d which is curved inward as in the case of the groove 13b in the bottom member 13a such that it conforms to the curvature of the mounting surface of the tube 4.

The body fluid processing circuit of the invention has the following advantages.

(1) Since the outer peripheral surface of the hole formed in the mounting surface of the main tube is curved upward (i.e., toward the mounting surface), blood can maintain a laminar flow through the main tube without forming any residue or experiencing any other troubles that frequently occur in the prior art due to blockage.

(2) The hole mentioned in (1) can be formed both at the site of connection to a branchline tube and at the site of formation of a mixing/injecting portion by the same method at the same time and in a positive manner.

(3) The bottom surface of the tubular member is welded to the tube with suction being applied and this ensures the bottom surface of the tubular member to be firmly welded to the mounting surface of the tube.

Figure 35:
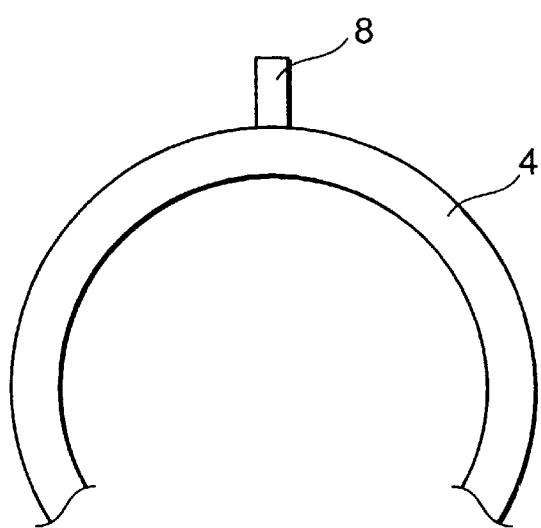
FIG. 35 is a schematic diagram of the body fluid processing circuit in use condition.
Figure 36:
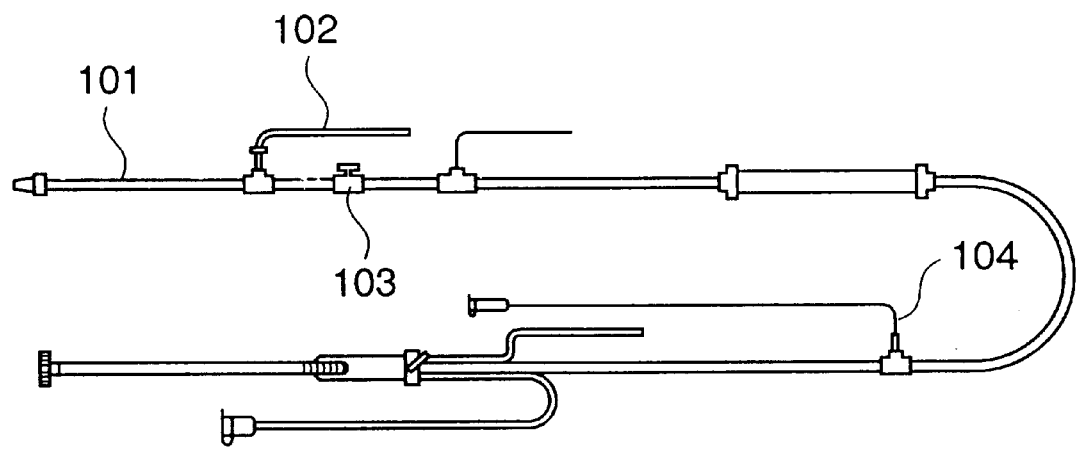
FIG. 36 is a schematic diagram of a prior art body fluid processing circuit.
Figure 37:
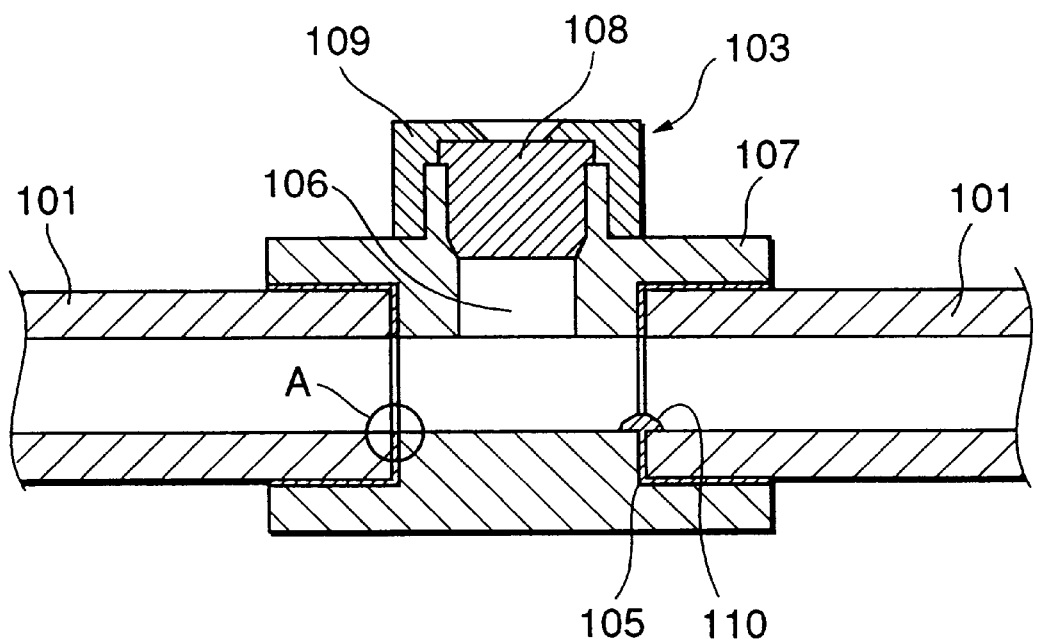
FIG. 37 is a partial enlarged view of the mixing/injecting portion in FIG. 36.
Figure 38:
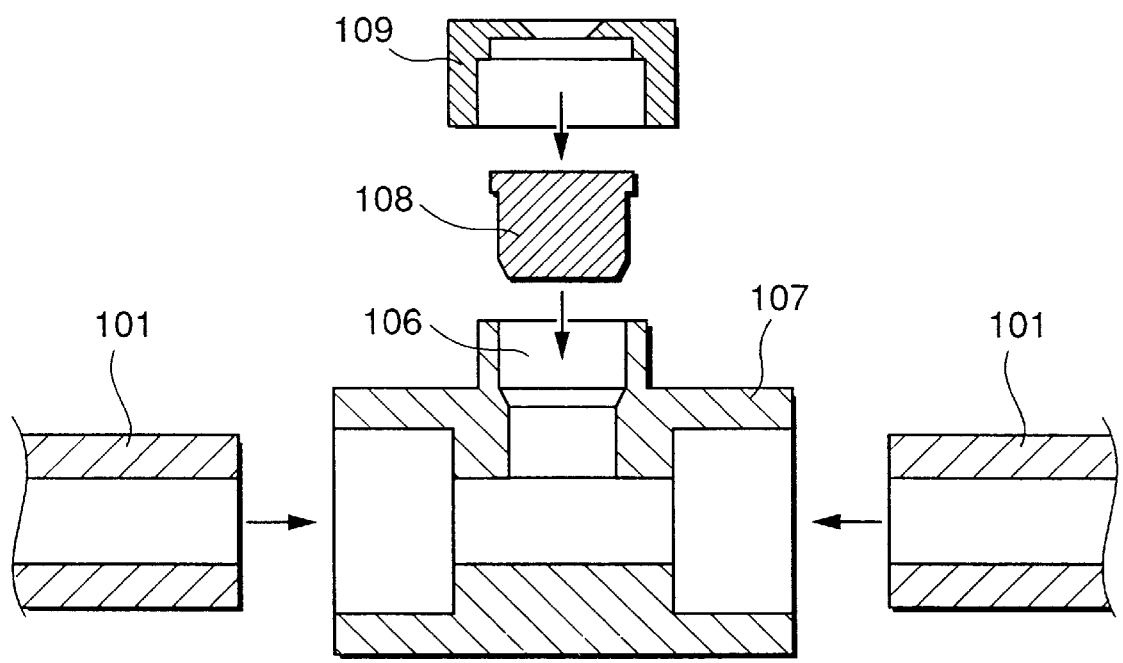
FIG. 38 is a schematic diagram illustrating how the mixing/injecting portion in FIG. 37 is assembled.
Figure 39:
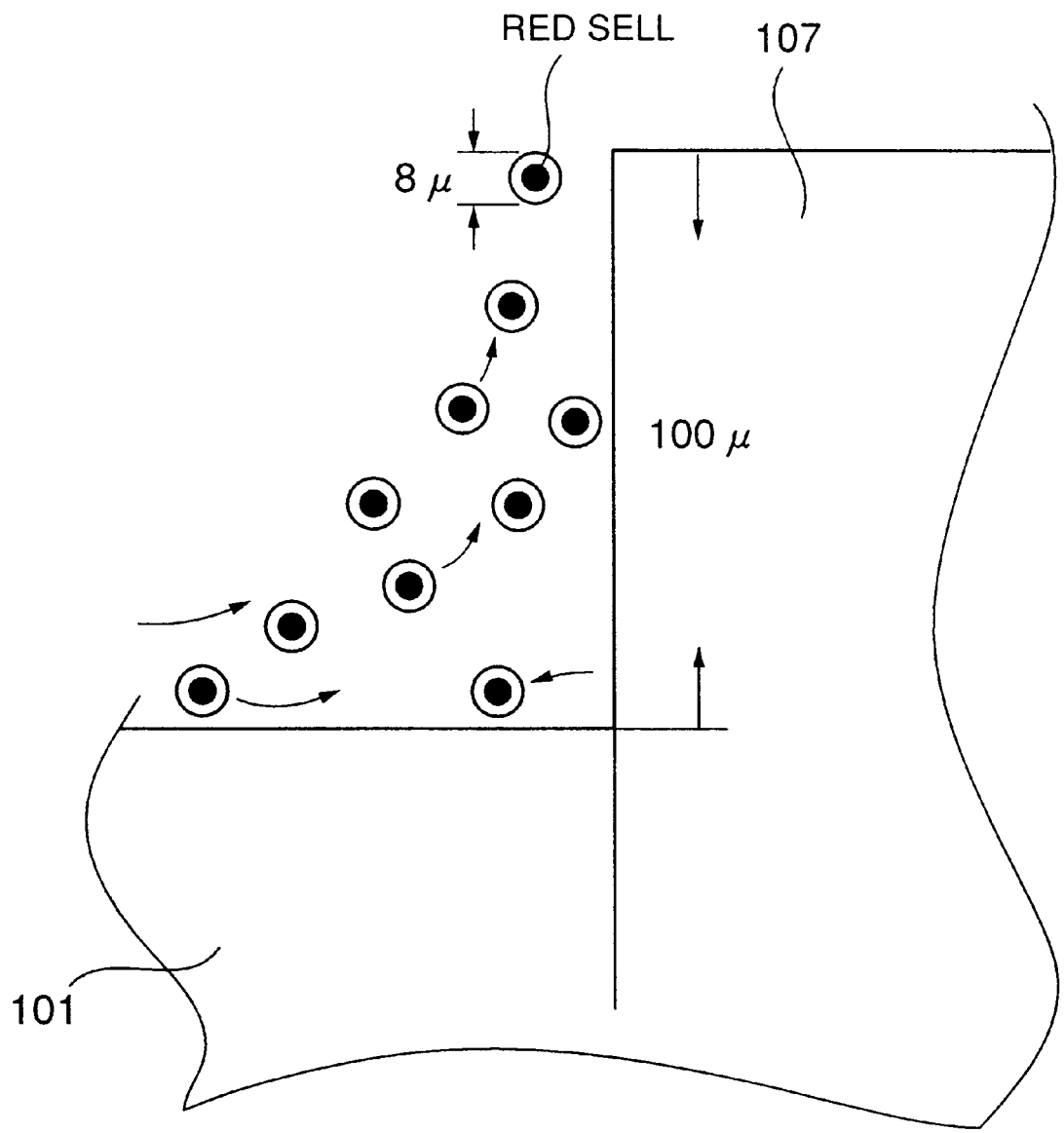
FIG. 39 is a partial enlarged view of FIG. 37.
Figure 40:
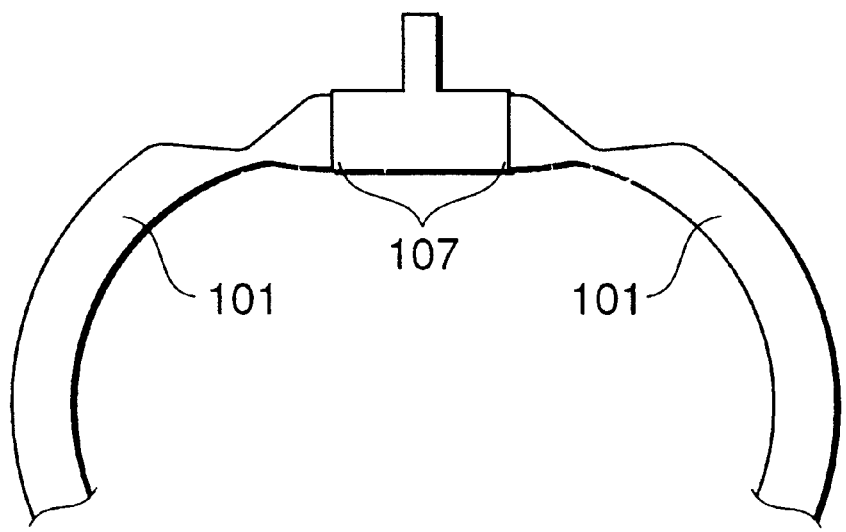
FIG. 40 is a schematic diagram of the prior art body fluid processing circuit in use condition.
Figure 41:
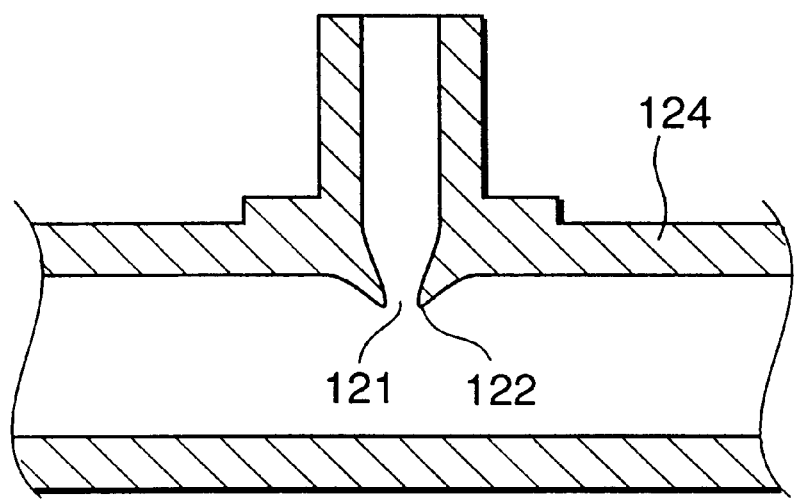
FIG. 41 shows an enlarged area around the branchline tube in the prior art body fluid processing circuit.

(4) Because of (3), although the body fluid processing circuit can be bent in areas near the tubular member during use, as shown in FIG. 35, the kink are less likely to develop in the main tube and, hence, an efficient operation is achieved.

(5) The main tube need not be cut to provide branches and this leads to a marked improvement in process efficiency.

(6) In the absence of seams along the length of the main tube, the problems that frequently occur in the related art such as blood coagulation, residual blood and hemolysis are eliminated are solved, and even if the addition of heparin to blood is reduced, it can be maintained in a state very close to the blood circulation in the human body.

(7) The hole to be formed in the mounting surface of the main tube can be reduced in diameter by a sufficient amount to eliminate the chance of blood coagulation, residual blood, homolysis and other troubles to occur in areas around the hole.

(8) Those portions which correspond to the interior of the body fluid processing circuit from the ambient atmosphere throughout the process of its manufacture starting with the extrusion of respective components and ending with the construction of a final assembly and, hence, complete aseptic and dust-free manufacture of the body fluid processing circuit can be realized.

(9) Since the heated tubular member is welded to the main tube being extruded at a comparably high temperature, the former can be mounted easily on the latter and yet firm fixing can be accomplished.

(10) Since no solvents are used, the solvent problem frequently encountered in the related art due to solvent dissolution in the blood and subsequent potential circulation in the human body can be totally eliminated to secure high hygiene and safety features.

What is claimed is:

1. A medical device having branches, which comprises:

a first tube formed in a straight form, said first tube being seamless along its length; and a second tube welded firmly to a mounting surface of said first tube;

wherein a hole is formed in said first tube so as to communicate with said second tube; and the outer peripheral surface of said hole is curved toward the mounting surface of said first tube.

2. The medical device according to claim 1, which further includes at least one of a branchline tube connected to a top of said second tube and a plug pressed into said second tube, to thereby form a processing portion.

3. The medical device according to claim 1, which further includes a bottom member mounted on an opposite side of said first tube to said second tube provided on said mounting surface of said first tube.

4. The medical device according to claim 1, wherein said second tube is welded at right angles to said first tube.

5. The medical device according to claim 1, wherein said second tub is welded at an angle to said first tube.

6. The medical device according to claim 2, wherein said second tube has a groove to which said branchline tube is connected without steps between said second tube and said branchline tube.

* * * * *